United States Patent
Gupta et al.

(10) Patent No.: US 10,207,002 B2
(45) Date of Patent: Feb. 19, 2019

(54) SUSTAINED RELEASE FORMULATION AND TABLETS PREPARED THEREFROM

(71) Applicant: Merck Sharp & Dohme Corp., Rahway, NJ (US)

(72) Inventors: Pranav Gupta, Springfield, NJ (US); David Monteith, Pittstown, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/577,636

(22) PCT Filed: Jun. 21, 2016

(86) PCT No.: PCT/US2016/038456
§ 371 (c)(1),
(2) Date: Nov. 28, 2017

(87) PCT Pub. No.: WO2016/209787
PCT Pub. Date: Dec. 29, 2016

(65) Prior Publication Data
US 2018/0154000 A1    Jun. 7, 2018

Related U.S. Application Data

(60) Provisional application No. 62/185,175, filed on Jun. 26, 2015.

(51) Int. Cl.
| | | |
|---|---|---|
| A61K 47/32 | (2006.01) |
| A61K 47/38 | (2006.01) |
| A61K 47/34 | (2017.01) |
| A61K 47/12 | (2006.01) |
| A61K 47/10 | (2017.01) |
| A61K 9/20 | (2006.01) |
| A61K 31/519 | (2006.01) |
| A61K 9/24 | (2006.01) |

(52) U.S. Cl.
CPC ............... *A61K 47/32* (2013.01); *A61K 9/20* (2013.01); *A61K 9/209* (2013.01); *A61K 9/2027* (2013.01); *A61K 9/2031* (2013.01); *A61K 9/2054* (2013.01); *A61K 31/519* (2013.01); *A61K 47/10* (2013.01); *A61K 47/12* (2013.01); *A61K 47/34* (2013.01); *A61K 47/38* (2013.01)

(58) Field of Classification Search
USPC ........................................................ 514/248
See application file for complete search history.

(56) References Cited

FOREIGN PATENT DOCUMENTS

| WO | WO2013067199 | 5/2013 | |
|---|---|---|---|
| WO | WO-2013067199 A2 * | 5/2013 | ........... A61K 31/381 |
| WO | WO2014072881 | 5/2014 | |
| WO | WO-2014072881 A1 * | 5/2014 | ........... C07D 491/04 |

OTHER PUBLICATIONS

Harris, Potent and selective adenosine A2A receptor antagonists [1,2,4]-triazole[4,3-c]pyrimidin-3-ones, Bioorganic Medical Chemistry Letters, 2011, 2497-2501, 21.
NPL—WrittenOpinion—PCTUS201638456—dated—Sep. 14, 2016.

* cited by examiner

*Primary Examiner* — Yong L Chu
(74) *Attorney, Agent, or Firm* — Keith D. MacMillan; Catherine D. Fitch

(57) ABSTRACT

Disclosed are formulations and tablets made therefrom comprising the compound of Formula IA or Formula IB which have sustained-release properties, and the dispersion containing the compounds of Formula IA or IB which facilitates such sustained release: Formula IA, Formula IB.

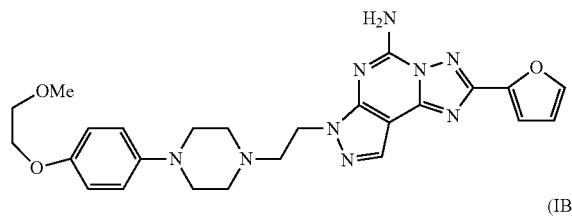

(IA)

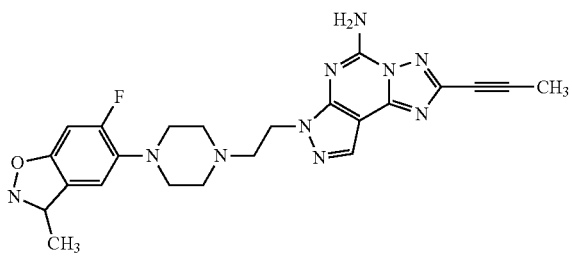

(IB)

13 Claims, 5 Drawing Sheets

Test A = CR 12 hr form, fasted (2x5mg)
Test B = CR 24 hr form, fasted (2x5mg)
Test C = IR/CR form, fasted (10mg)
Reference D = IR form, fasted (10mg)

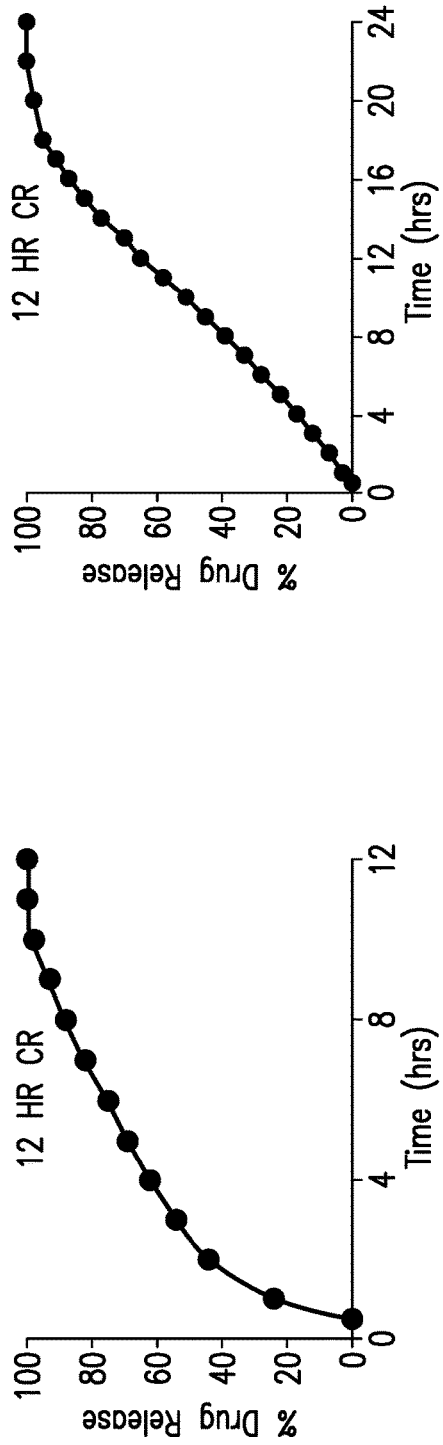
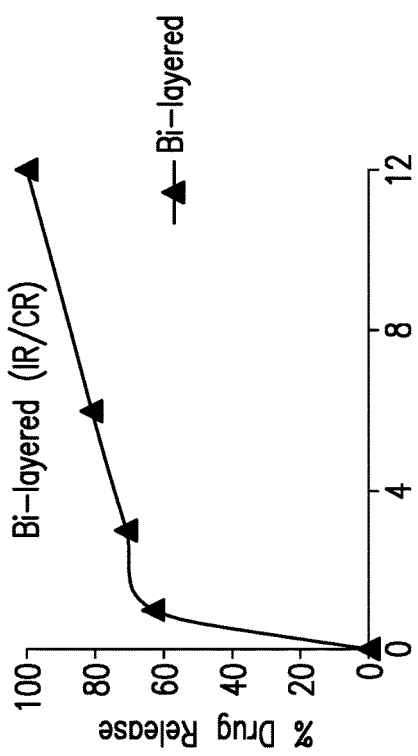
FIG. 3A
FIG. 3B
FIG. 3C

SUSTAINED RELEASE FORMULATION AND TABLETS PREPARED THEREFROM

CROSS-REFERENCE TO RELATED APPLICATIONS

This application is a U.S. National Phase application under 35 U.S.C. § 371 of PCT Application No. PCT/US2016/038456. filed Jun. 21, 2016, which claims the priority of U.S. Provisional Application Serial No. 62/185, 175, filed on Jun. 26, 2016, each of which applications are incorporated herein by reference.

BACKGROUND

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Selective antagonists for the $A_{2A}$ receptor are of pharmacological interest because of their reduced level of side affects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in WO 95/01356; U.S. Pat. No. 5,565,460; WO 97/05138; and WO 98/52568.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-Dopa, directly through stimulation of the post-synaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-Dopa (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds which are $A_{2A}$ receptor antagonists are believed to be useful in alleviating motor symptoms associated with Parkinson's disease. For example, U.S. Pat. No. 6,630,475 to Neustadt et al. (the '475 patent) describes the preparation of the compound of Formula PI:

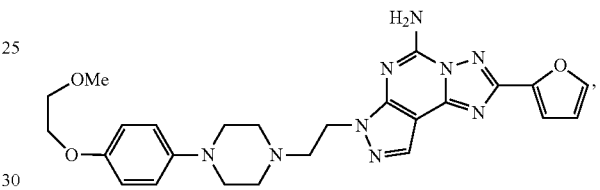

Formula IA

In the '475 patent example Schemes 1 to 5, along with preparative Schemes 1 to 4, show general methods of preparing compounds of Formula IA. The '475 patent describes also that the compound of Formula I can be prepared as a pharmaceutically acceptable salt which may be useful for treating Parkinson's disease.

Another example, U.S. Pat. No. 8,389,532 to Boyle et al. (the '532 patent) describes the preparation of the compound of Formula IB:

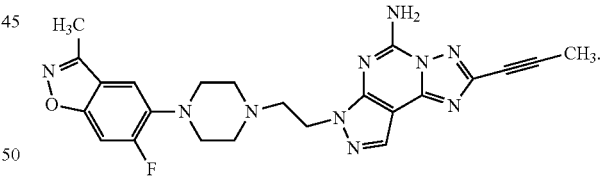

Formula IB

The compounds of Formulae IA and IB are both poorly soluble in a basic environment, such as the intestine, and in particular, when the compound of Formula I is co-administered with a proton-pump inhibitor a sharp drop in bioavailability has been observed.

The use of $A_{2A}$ receptor antagonists, for example, those of Formulae IA and IB requires a dosage form providing an ability to administer the compound to a patient in need thereof and desirably, the dosage form will afford dosage periodicity that minimizes the number of times it must be administered in a given period. Such dosage forms are believed to provide improved compliance and effect improved therapeutic outcome by minimizing therapeutic compound serum peak and trough levels and providing desired trough conc's of the drug at specific times (e.g C12 or C24 trough conc's) and/or exposure levels of the drug that is comparable to the more frequently administered immediate release dosage forms which are believed to have value in the treatment of central nervous system disorders, in particular treating or managing the progression of such diseases, for example, but not limited to, Parkinson's disease.

Solid dispersions, and, particularly, solid solutions, have been employed to promote the oral absorption of poorly water soluble active pharmaceutical ingredients (APIs), see, for example, Ford, Pharm Acta Helv, 1986, 61:69-88. Solid dispersions and solid solutions are compositions in which API is dispersed into or dissolved in a solid matrix, generally a polymer matrix. Solid solutions and solid dispersions (in which the active pharmaceutical ingredient forms a homogeneous or nearly homogeneous glass in the excipient matrix) are of particular interest in the oral delivery of poorly water soluble compounds. It is believed that these materials improve the absorption of orally administered API by improving: (i) the wetting properties of the API; (ii) causing at the point of absorption transient supersaturation of the API with respect to a lower energy (e.g. crystalline) phase API; or (iii) both effects. In general, solid solutions are believed to enable drug absorption by enhancing the dissolution rate and/or the extent to which the drug is dissolved from the matrix.

One example of a Class II drug which has been formulated as a solid solution is posaconazole, as described in International Patent Application, publication no. WO2009/129300, published Oct. 22, 2009. Such compositions of posaconazole were prepared by forming an extrudate of posaconazole in hydroxypropylmethylcellulose acetate-succinate-derivatized polymer (HPMC-AS), which solid dispersion was subsequently blended with microcrystalline cellulose, additional HPMC-AS, hydroxypropylcellulose, and magnesium sterate. This admixture was tableted to provide an orally bioavailable posaconazole formulation with desirable PK and bioavailability.

Another example of polymers employed in providing a solid solution of polymer and API is reported by Goertz et al. in U.S. Pat. No. 4,801,460 describes solid dispersions comprising a poorly soluble drug (exemplified by theophylline) and cross-linked polyvinylpyrrolidone/vinyl acetate copolymer (PVP copolymer). The '460 patent reports drug release times of up to 8 hours in tests employing such polymer matrix solid solutions.

In another example, Fry et al. describe formulations of HER-2 inhibitors dispersed in a wide variety of polymer matricies, including many different derivatives of cellulosic polymers (including graft copolymers incorporating cellulosic moieties), polyvinyl alcohol polymers and polyvinylpyrrolidine polymers. See published international application publication no. WO2013/056108, published Apr. 18, 2013. Such compositions are said to reduce interpatient PK variability.

Despite their growing use, the design of solid solution formulations to effectively promote oral drug absorption remains largely a matter of trial and error. Successful formulation of lipophilic compounds as solid dispersions to promote oral absorption may benefit from a strong interaction between API and polymer. This has led to interest in partially water soluble polymers with amphiphilic properties like hydroxypropyl methylcellulose acetate succinate (HP-MCAS), especially when the process used to create the solid dispersion is spray drying. See Friesen et al., Mol. Pharm., 2008, 5:1003-1019. While this approach was successful for many drug candidates, it was suggested that compounds with high melting points (or high ratios of melting point to glass transition temperature) and/or particularly lipophilic compounds (e.g., those with high log P values) are especially problematic to successfully formulate as solid solutions. Friesen et al. suggests that successful formulations of compounds having high melting point properties will likely be limited to relatively dilute concentrations of API in the solid dispersion.

In another report, controlled-release indomethacin-containing acrylic-based polymer dispersion formulations prepared by hot-melt extrusion (HME) using Eudragit® RD-100 in combination with one or more of Eudragit® L-100, Eudragit® S-100 or Eudragit® RE-100 to modify release rates have been prepared (Drug Development and Industrial Pharmacy, 2006 (32) pp 569 to 583), however this report indicates that formulations containing 51 wt. % Eudragit® RD100 and 10 wt. % Eudragit® S-100 exhibit release that in acid environments are unacceptable low and in neutral environments approach immediate release profiles (see FIG. 9 C therein).

Some studies have demonstrated dosage forms based upon acrylate polymers which undergo slow degradation in the environment in which the active is to be released, for example, for example, the previous study cited using Eudragit® RD 100, however, no controlled release formulations have been demonstrated which provide the desired trough concentrations and exposure levels necessary to provide a once-daily (QD) dosage form for compounds of Formula I or Formula II.

SUMMARY OF THE INVENTION

In one aspect, the invention provides an amorphous dispersion which supplies an effective amount of an A2a-antagonist, wherein said amorphous dispersion comprises up to about 8 wt % API, preferably from about 4 wt. % to about 8 wt. % of API, up to about 30 wt. % of plasticizer wherein the plasticizer is optionally a mixture of plasticizer and co-plasticizer, and the balance matrix polymer. In some embodiments wherein the plasticizer used is a mixture of plasticizer and co-plasticizer, the mixture is preferably from about 20 wt. % to about 30 wt % plasticizer with from about 0.5 wt % to about 10 wt. % of the optional co-plasticizer. In some embodiments the amorphous dispersion is preferably made by hot-melt extrusion of the blended constituents.

In some embodiments, preferably the API in the amorphous dispersion is a compound of Formula I shown in Table I, or a salt thereof:

TABLE I

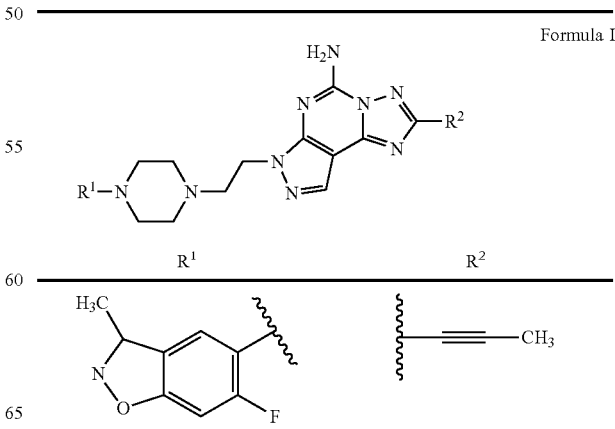

TABLE I-continued

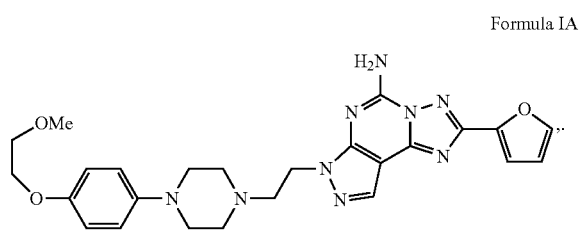 [SMILES: COCCOc1ccc(N2CCN(CCn3ncc4c3nc(N)n3nc(-c5ccco5)nc43)CC2)cc1]

In some embodiments it is preferred for the compound of Formula A to be the compound of Formula IA, or a salt thereof:

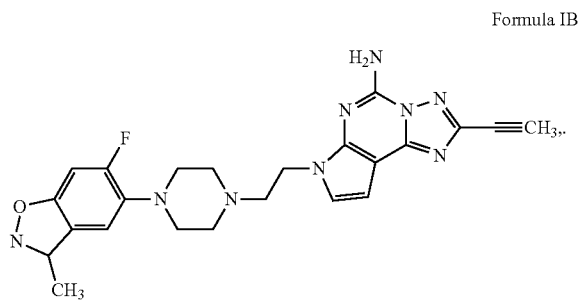

In some embodiments it is preferred for the compound of Formula I to be the compound of Formula IB, or a salt thereof:

Formula IB

In some embodiments, preferably the matrix polymer in the amorphous dispersion is a polymer made from free-radical polymerization of methacrylic acid and methylmethacrylate in a 1:2 ratio, and having an average molar mass of approximately 125,000 g/mol. In some embodiments the matrix polymer in the amorphous dispersion is preferably a polymer made from free-radical polymerization of methacrylic acid and ethylacrylate in a 1:1 ratio, and having an average molar mass of approximately 320,000 g/mol.

In some embodiments it is preferred for the plasticizer to be triethylcitrate. In some embodiments it is preferred for the plasticizer to be a mixture comprising from about 1:2 wt./wt. citric acid/triethyl citrate, to about 98.4 wt. % triethyl citrate/1.6 wt. % citric acid.

In some embodiments, preferably the amorphous dispersion comprises up to the components shown below in the weight ratios described in Table II:

TABLE II

| Constituent | Identity | Weight percent of total |
| --- | --- | --- |
| Active Pharmaceutical Ingredient (API) | Compound of Formula I | 5.0 wt % |
| Matrixpolymer | Poly(methacrylic acid/methylmethacrylate 1:2 ratio)/ Methacrylic Acid Copolymer Type B, NF (Eudragit S-100) | 70 wt. % |
| Plasticizer | Triethylcitrate | 25 wt. % |

In some embodiments, preferably the amorphous dispersion comprises up to the components shown below in the weight ratios described in Table III:

TABLE III

| Constituent | Identity | Weight percent of total |
| --- | --- | --- |
| Active Pharmaceutical Ingredient (API) | Compound of Formula I | 4.0 wt % |
| Matrixpolymer | Poly(methacrylic acid/methylmethacrylate 1:2 ratio)/ Methacrylic Acid Copolymer Type B, NF (Eudragit S-100) | 68 wt. % |
| Plasticizer | Triethylcitrate | 28 wt. % |

In some embodiments it is preferred to blend a dispersion of the invention with other excipients to provide a formulation which is suitable for pressing a tablet. In some embodiments, preferably, a tablet formulation comprises, in addition to an aliquot of a dispersion of the invention, a controlled release polymer, a precipitation inhibitor and a diluent.

In some embodiments it is preferred to provide a formulation which can be pressed into a tablet that comprises about 5 mg of API in a tablet weight of 475 mg. In some embodiments it is preferred to provide a formulation which can be pressed into a tablet that comprises about 5 mg of the API with a tablet weight of 575 mg. In some embodiments it is preferred to provide a formulation which can be pressed into a tablet that comprises about 5 mg of API in a tablet weight of 475 mg. In some embodiments it is preferred to provide a formulation which can be pressed into a tablet that comprises about 5 mg of the API with a tablet weight of 600 mg. In some embodiments it is preferred for 5 mg tablet formulations to provide a therapeutic serum level for a period of at least about 12 hours.

In some embodiments, it is preferred to combine an aliquot of a tablet formulation of the invention with an aliquot of an immediate-release Formulation, thus providing a combination dosage formulation which contains a total of about 10 mg of API in a tablet weight of 675 mg. In some embodiments, it is preferred to combine an aliquot of a tablet formulation of the invention with an aliquot of an immediate-release Formulation, thus providing a combination dosage formulation which contains a total of about 10 mg of API in a tablet weight of 700 mg. In some embodiments it is preferable to provide the combination dosage form as a bilayer tablet In some embodiments it is preferred for 10 mg tablet formulations to provide a therapeutic serum level for a period of at least about 24 hours.

In some embodiments it is preferred for immediate release Formulation C to comprise the Formulation of Table III:

TABLE IV

| Constituent | Wt % (finished formulation) |
|---|---|
| API (compound of Formula PI) | 2.5 wt. % |
| Granulated constituents | |
| Microcrystalline cellulose | 9.0 wt % |
| Mannitol | 64.8 wt % |
| PVP | 2.5 wt % |
| Croscarmellose sodium | 2.5 wt % |
| Constituents mixed with granulate | |
| Microcrystalline cellulose | 16.0 wt % |
| Croscarmellose sodium | 2.5 wt % |
| Magnesium Stearate | 0.2 wt % |
| | 100.0 |

In some embodiments it is preferred to provide a bilayer tablet comprising up to about 200 mg of the immediate-release formulation of Table III and up to about 500 mg of a sustained-release formulation of the invention.

In some embodiments, it is preferred to administer a tablet which provides the dissolution profile of FIG. 3A, 3B, or 3C and the AUC and Cmax parameters shown in Table IV.

TABLE V

| PK Parameter | IR Tablet (Reference) (5 × 2 = 10 MG) | CR-12 Hr Tablets (5 × 2 = 10 MG) | CR-24 Hr Tablets (5 × 2 = 10 MG) | Bilayer IR/CR Tablet (10 MG) |
|---|---|---|---|---|
| No. of subjects (N) | 16 | 15 | 14 | 14 |
| AUC 0-24 (ng · hr/mL) | 557.60 | 370.30 | 298.77 | 472.64 |
| Cmax (ng/mL) | 167.02 | 58.40 | 35.24 | 77.80 |
| C24 (ng/mL) | 2.54 | 6.71* | 9.21* | 4.07* |
| Tmax (hr) | 1 | 3.0 | 4.5 | 1 |
| T½ (hr) | 6.79 | 15.8* | 11.9* | 11.4* |

In some embodiments it is preferred to administer a sufficient quantity of formulation of the invention, preferably in the form of a tablet or a bilayer tablet, to provide a therapeutically effective serum level in the management of a neurological movement disorder. In some embodiments the neurological movement disorder for which management is sought is preferably related to Parkinson's disease.

BRIEF DESCRIPTION OF THE DRAWINGS

FIG. 3: In vitro Dissolution Profile of Tablets of the Invention;

DETAILED DESCRIPTION OF THE INVENTION

Figure 1:
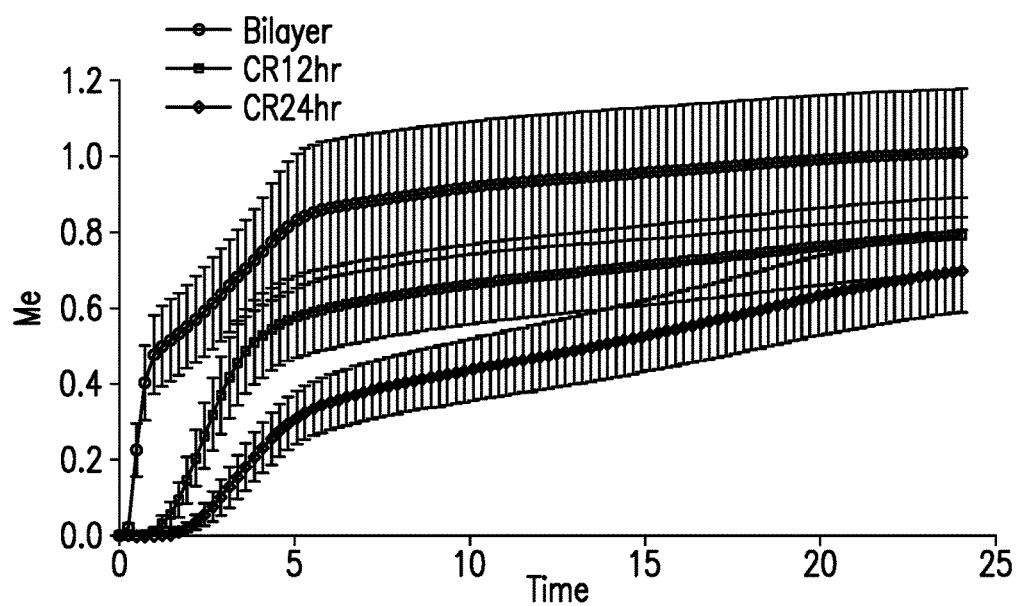
FIG. 1: Calculated In Vivo Drug release profiles from tablets of the invention obtained by deconvolution of PK profiles relative to data obtained from an immediate release formulation.

The following terminology, which may be used herein, is used in accordance with the following definitions.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between.

The term "formulation", as used herein, refers to a blend, aggregation, solution or other combination of materials which includes an active pharmaceutical ingredient (API) which formulation may be adapted to a particular mode of administration by methods known to those of ordinary skill in the art, for example, a formulation suitable for pressing into tablets designed for oral administration, in the treatment, management, prevention and etc. of a disease state or condition in a patient.

The term "subject" as used herein refers to an animal, preferably a mammal, most preferably a human, who has been the object of treatment, observation or experiment. When a human subject suffering from the condition to be treated is included in the activity they are alternatively referred to herein as a "patient".

The following definitions apply to excipients which may be used in formulations of the invention as the terms are used herein:

A diluent is an excipient which increase the bulk of a dosage form, typically where the active pharmaceutical ingredient in the formulation is too potent to permit convenient processing or administration of a dosage form which does not include a diluent, or where the formulation by itself without a diluent makes formation of the dosage form difficult (for example, where an aliquot of the formulation without a diluent would be of too small of a volume to form the aliquot into a tablet);

A disintegrant is an excipient that expands and/or dissolves when placed in an aqueous environment, for example, the gastrointestinal tract, which aids a tablet in breaking apart and promotes release of an active pharmaceutical ingredient contained in a tablet;

A Glidant is an excipient, for example colloidal silica, that enhances the flow of a granular mixture by reducing interparticle friction.

A Binder is used to impart cohesive qualities to a tablet, aid thus ensure that the tablet remains intact after compression.

A nucleation inhibitor is an excipient, for example, a polymer such as HPMCAS (AQOAT from Shin-Etsu) that prevents crystal nucleation or crystal growth thereby preventing conversion of the amorphous drug to the insoluble crystalline form of the drug through the course of drug release from the formulation.

A plasticizer is a substance or blend of substances which when added to a polymer modifies some thermal or physical property of the polymer.

Stabilizers, as well known in the art, are used to inhibit or retard drug decomposition reactions that include, by way of example, oxidative reactions which in this case will be termed as an antioxidant.

As mentioned above, the present invention is directed to composition which is an amorphous dispersion comprising a soluble polymer matrix and dispersed or dissolved therein a compound of Formula A, or a salt thereof, wherein $R^1$ and $R^2$ are selected from those variable shown in Table I:

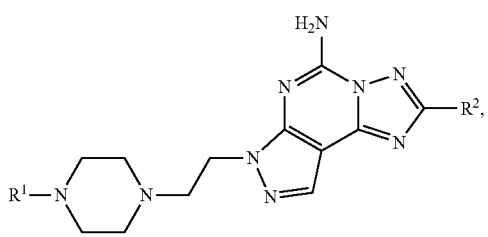

or a salt thereof, wherein $R^1$ and $R^2$ are defined herein.

Compounds of Formula I suitable for use in compositions of the invention may be prepared in accordance with the synthesis described in, for example, U.S. Pat. No. 6,630,475 (compound of Formula IA) and U.S. Pat. No. 8,389,532 (compound of Formula IB).

Figure 4:
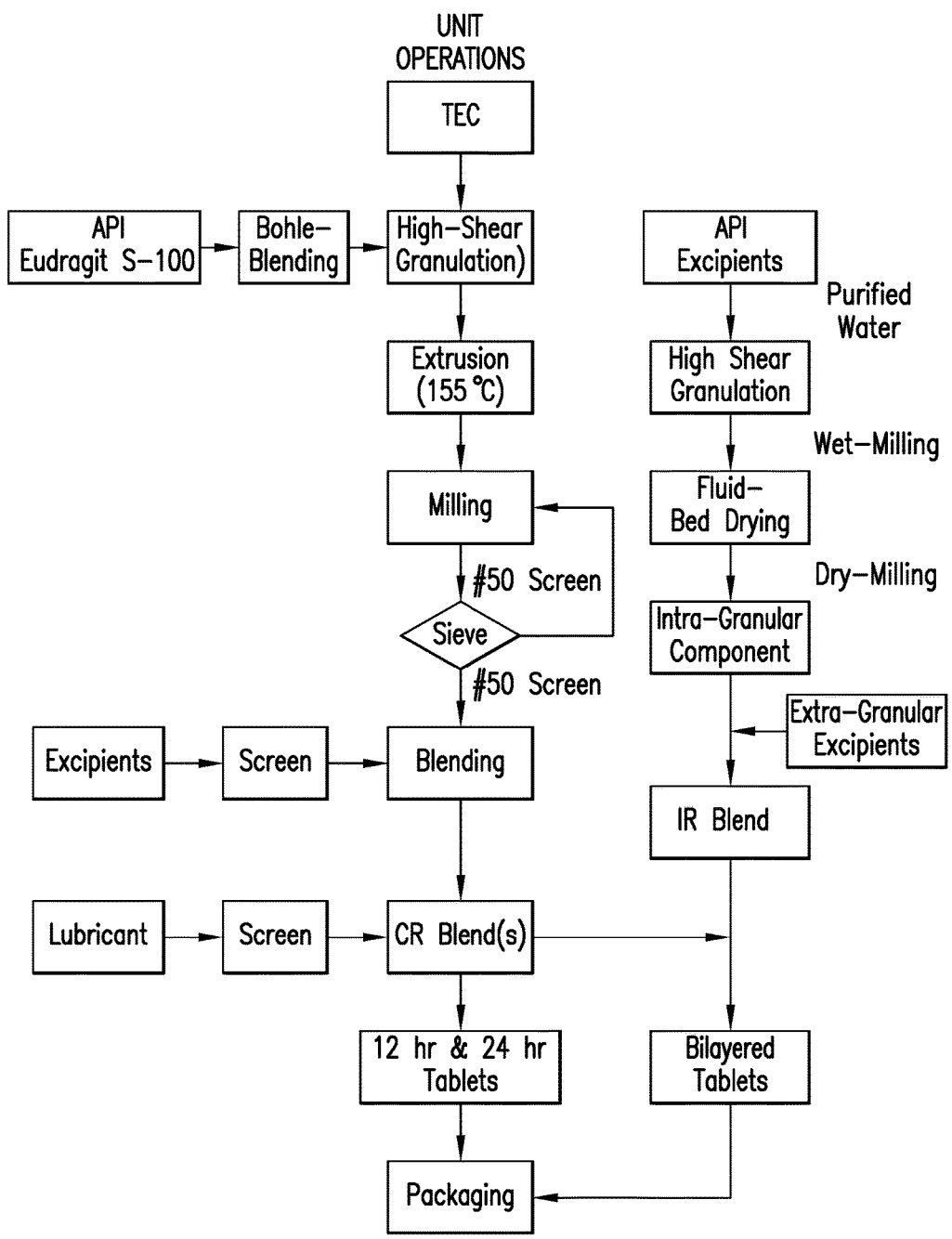
FIG. 4: Flow Chart Illustrating Unit Operations in Formulating Tablets of the Invention.

In some embodiments it is preferred to prepare dispersions of the invention by hot melt extrusion of the constituents (HME), in which event the dispersion is referred to also as an extrudate. With reference to FIG. 4, in general the extrudate may be prepared by hot-melt extrusion (HME) of a blend of a compound of Formula I, the matrix polymer, which is preferably an anionic polymer made from free-radical polymerization of a particular ratio of methacrylic acid and either methylmethacrylate or ethylacrylate, and various excipients which may or may not have received additional operations to render them suitable for HME processing.

The inventors have found that anionic polymers do not generally provide a suitable dispersion of a Class II drug to effectively provide a stable supersaturated solution of the drug and matrix polymer to the GI tract. Surprisingly, when a dispersion is prepared from certain polymethacrylic acid-based copolymers, administration of such a dispersion, in conjunction with a precipitation inhibitor, provides a stable supersaturated solution to the GI tract. One example of a suitable dispersions is a dispersion prepared using the compound of Formula IA as active pharmaceutical ingredient (API) dispersed in a 1:1 polymethacrylic acid/ethylacrylate copolymer (i.e. Eudragit® L-110-55) polymer matrix. Another example of a suitable dispersions is a dispersion prepared using the compound of Formula IA as active pharmaceutical ingredient (API) dispersed in a 1:2 methacrylic acid and methyl methacrylate matrix polymer (i.e. Eudragit® S-100).

When polymer dispersions of the invention are formulated in combination with a controlled release polymer and a precipitation inhibitor and administered to the GI tract, there is provided thereby a stable supersaturated solution of the API which releases the API in a sustained manner. When tested in a simulated GI environment formulations of the invention indicated that in vivo they provide: (i) consistent bioavailability and serum levels; and (ii) acceptable AUC curves to afford sustained therapeutic serum levels when tested under the same conditions (see FIGS. 4, 2B and 3A to 3C). Moreover, when formulations using this dispersion system were tested in vitro, it was found that the dispersion could provide controlled drug release over 20 hours without significant drug precipitation (crystallization)

Accordingly, formulations of the invention comprise a compound of Formula I (described above), preferably a compound of Formula IA or Formula IB dispersed in a selected anionic matrix polymer. In some embodiments, the preferred anionic polymer is one that is prepared by free-radical polymerization of a 1:2 mixture of methacrylic acid and methylmethacrylate or a matrix polymer that is prepared by free-radical polymerization of a 1:1 mixture of methacrylic acid and ethylacrylate.

In some embodiments, for dispersions prepared using a matrix polymer prepared from a 1:2 mixture of methacrylic acid and methylmethacrylate, preferably, the matrix polymer has a weight average molecular mass of approximately 125 Kg/mol. An example of a suitable commercially-available polymer is known as CAS number: 25086-15-1, which is known by the IUPAC name of Poly(methacylic acid-co-methyl methacrylate) 1:2, and is commercially available under the trade name Eudragit® S-100.

In some embodiments, for dispersions prepared using a matrix polymer prepared from free radical polymerization of a 1:1 mixture of methacrylic acid and ethylacrylate, preferably the matrix polymer has a weight average molecular mass of approximately 320 Kg/mol. An example of a commercially-available suitable polymer of this type is USP/NF designation Methacrylic Acid Copolymer, Type C-NF which is sold under the trade name Eudragit® L 100-55. Other suitable polymers that are commercially available are, for example HPMCP or HPMCAS from Shin-Etsu. As the term is used herein, average molecular mass is as determined by the manufacturer of Eucragit® L 100-55 and S-100

Dispersions used in formulations of the invention contain also a plasticizer, which, as mentioned above, is an excipient which modifies some physical or thermal property of a polymer. Without being bound by theory, it is believed that for use in the invention a plasticizer reduces the thermal energy required to drive a compound of Formula I into solution in the matrix polymer and promote formation of the dispersion. For extrudates of the invention, in some embodiments it is preferred to employ as a plasticizer an ester of citric acid, for example, triethylcitrate. In some embodiments a preferred plasticizer is a combination of triethylcitrate plasticizer and a coplasticiser mixture of citric acid/stearic acid. It will be appreciated that other plastacisers and combinations of plasticisers and coplasticisers may be employed, for example, stearic acid (Sigma-Aldrich), triacetin (Eastman/Sigma-Aldrich), d-alpha-tocopheryl polyethyleneglycol succinate (vitamin E TPGS from Eastman); and high molecular weight polyethylene glycol polymers, for example PEG 3350 from Sigma Aldrich.

In dispersions of the invention utilizing a mixture of citric acid and triethyl citrate as a plasticizer, in some embodiments the plasticizer mixture comprises from about 1:2 wt./wt. citric acid or stearic acid/triethyl citrate, to about 98.4 wt. % triethyl citrate/1.6 wt. % citric acid/stearic acid. In some embodiments, preferably the plasticizer is triethyl citrate alone.

In some embodiments a dispersion of the invention comprises at least about 4 wt. % of a compound of Formula I up to about 8 wt. % of a compound of Formula I, preferably from about 4 wt. % up to about 6 wt. % of a compound of Formula I, from about 20 wt. % to about 30 wt. % of a plasticizer or a plasticizer/coplasticiser mixture preferably from about 22% w % up to about 28% wt %, and the balance a matrix polymer comprising an methacrylic acid/methylmethacrylate 1:2 copolymer. In some embodiments, a formulation of the invention also contains one or more surfactants, for example, SDS Cremophors® (BASF, various grades), polysorbates (various grades), Solutol® from BASF, Gelucires® from BASF, Spans (various grades), PEG (1-10% w/w).

Dispersions of the invention may be prepared by processes that are suitable for causing the selected API (for example, a compound of Formula IA) to form a dispersion throughout the polymer matrix such that the drug is generally an amorphous uniform dispersion in the polymer or dissolved in the polymer. In general this requires some method of heating and mixing the constituents of the desired composition together and recovering the dispersion or solution in a solid form. Although it will be appreciated that any means affording a dispersion may be employed without departing from the invention, in some embodiments it is preferred to prepare compositions of the invention via Hot Melt Extrusion (HME). Hot melt extrusion (HME) is a technique in which an extruder, for example, an 18 mm ZSE mm Leistritz twin screw extruder, is employed to blend and heat the polymer, drug, and dispersing agent, whilst forming the finished composition dispersion or solution into a "noodle" or other conveniently handled shape which may be employed in further processing in the preparation of tableting formulations (extrudate).

In carrying out such operations, some or all of the components may be premixed prior to introducing them into the extruder, for example, by blending dry powders or wet milling or wet mixing, the constituents together in a blending, mixing or granulation process to insure intimately mixed constituents that lead to a homogeneous blend of constituents when the blend is fed into the extruder. Alternatively, the constituents may be fed into the extruder using independent feed streams (see Polymer Extrusion 4$^{th}$ Edition by Chris Rauwendaal 2001, Hanser Gardner Publications, Inc., Cincinnati, Ohio or Schenck et al., (2010), Achieving a Hot Melt Extrusion Design Space for the Production of Solid Solutions, in Chemical Engineering in the Pharmaceutical Industry: R&D to Manufacturing (ed. D. J. am Ende), John Wiley & Sons, Inc., Hoboken, N.J., USA). Although for some compositions of the invention it is preferred to employ an HME process to prepare them, it will be appreciated that compositions of the invention can be prepared by any means useful for preparing a melt in any convenient apparatus in which an admixture of a compound of Formula I, matrix polymer and dispersing agent can be heated, mixed, and recovered.

In general, when extruding materials, the act of transporting the material through the extruder results in imparting energy to the material, which is converted to heat in the transported material. When heat transfer from the extruder power consumed in material transport is not by itself sufficient to achieve the temperature required to produce the desired dispersion or solution of a compound of Formula I in the polymer matrix, generally the barrel of the extruder is provided with means to impart additional heat to the material. In like manner, different sections of the extruder barrel can be heated or cooled, as needed, to maintain a particular temperature within a section of the extruder barrel or even extract heat in a different section of the extruder barrel to cool the material as it is passing through. In general the extruder temperature, power and transport speed of the extruder are set to provide the minimum temperature excursion and residence time needed to insure that a homogeneous dispersion or solution is prepared, thus minimizing the amount of API that undergoes degradation during processing.

In general, the extrudate emerging from an extruder is in a plastic state and solidifies upon emerging from the barrel due to pressure release and cooling. During this transition, typically the extrudate has a profile shape, for example, noodles, bars, cylinders, etc., and is "cut" into convenient length pieces. Once extrudate pieces are obtained, they can be further mechanically processed to provide a convenient form for incorporation into a dosage form, for example, by milling, grinding, or sieving. As the term is used herein, the material emerging from the extruder, and any form into which that material is subsequently rendered by mechanical processes, for example, milling, grinding, blending, sieving or granulating, is termed the "extrudate". Exemplary extruders include those provided by Leistritz, for example an 18 mm or 27 mm Leistritz twin screw extruder, and those provided by Thermo-Fisher, for example, a 16 mm twin screw Thermo-Fisher extruder. This equipment is generally equipped with means of heating the extruder barrel permitting it to be used in a "hot melt extrusion" operation.

Once the extrudate is prepared it can be incorporated into a formulation for use in providing a dosage form suitable for oral administration, for example, a formulation adapted for pressing into tablets or filling into capsules. To achieve the dissolution and disintegration targets needed for effectively administering a compound of Formula I in the provision of treatment or management of movement disorders associated with Parkinson's Disease, a formulation is prepared which comprises the finished extrudate, preferably milled to provide a powdered form that is easily blended with the other constituents of the formulation. Accordingly, the milled extrudate is blended with at least one precipitation inhibitor, at least one controlled release polymer, and other excipients necessary or useful for providing a formulation suitable for use in pressing tablets, which may include, for example, preservatives/antioxidants, diluents, compression aids, disintegrants; precipitation inhibitors and/or lubricants.

In some embodiments of a formulation prepared using the finished extrudate, a controlled-release polymer is present in an amount which is preferably from about 10 wt. % of the final formulation to about 40 wt. % of the final formulation, more preferably from about 15 wt. % of the final formulation to about 30 wt. % of the final formulation. In some embodiments the controlled release polymer is present in a range of from about 15 wt. % of the final formulation to about 25 wt. % of the final formulation. In some embodiments of a formulation prepared using the finished extrudate, a precipitation inhibitor is present in an amount which is preferably from about 10 wt. % of the final formulation to about 40 wt. % of the final formulation, more preferably from about 20 wt. % of the final formulation to about 40 wt. % of the final formulation. In some embodiments the precipitation inhibitor is present in a range of from about 25 wt. % of the final formulation to about 35 wt. % of the final formulation.

For formulations of the invention, suitable controlled-release polymers, for example, a hydrophilic polymer, for example, but are not limited to a polyoxyetheylene oxide polymer; for example, commercially-available PEO-PolyOX N WSR Coagulant (Dow) or PolyOX N 60K (Dow) or combinations thereof. Other polymers which may be substituted in whole or part for a controlled-release polymer include different molecular weights of polyethylene oxide polymers, hydroxypropylmethylcellulose polymers and the following examples of commercially-available polymers: HPMC K4M, HPMC K15M; HPMC 100LV, HPMC K100M or combinations thereof (Dow), cellulosic polymers sold under the trade names Affinisol K4M (Dow) Benecel® (Ashland), Kollidon SR (80% of polyvinyl acetate and 19% povidone based sustained release polymer, BASF) and Eudragit RS/RL (Evonik).

Suitable precipitation inhibitors for tablet formulations of the invention include, but are not limited to, commercially available HPMC-AS from (Shin-Etsu, Ashland)

In some embodiments, a tablet formulation of the invention may contain also: a diluent (for example, mannitol, article of commerce, and/or microcrystalline cellulose, for example Avicel®); a binder (for example polyvinylpyrrolidone); a disintegrant (for example croscarmellose sodium); an antioxidant, for example, BHT; and a lubricant (for example, magnesium stearate) all articles of commerce. It will be appreciated that in formulating compositions of the invention, other diluents, glidants, and lubircants may be substituted or added to effect similar formulations.

Suitable diluents and fillers for use in tablet formulation of the invention include, for example, silicon dioxide, titanium dioxide, alumina, talc, kaolin, powdered cellulose, and microcrystalline cellulose, silicified microcrystalline cellulose, dicalcium phosphate, mannitol, urea, sucrose, lactose, lactose monohydrate, dextrose, sodium chloride, and sorbitol.

Suitable disintegrants for use in formulations of the invention include starches, cross-linked starches, clays, celluloses, cross-linked cellulose, sodium croscarmellose and low substituted hydroxypropyl cellulose (L-HPC), algins, gums, crosslinked polymers such as crosslinked poly vinyl pyrrolidone, for example, article of commerce Crospovidone, homopolymer of cross-linked N-vinyl-2-pyrrolidone, ion-exchange resin, and combinations of standard disintegrants, for example, a combination of sodium starch glycolate and alginic acid.

Suitable antioxidants for use in formulations of the invention include BHT. Suitable lubricants for use in formulations of the invention include magnesium stearate, calcium stearate, hydrogenated vegetable oil, sodium stearyl fumarate, and combinations of magnesium stearate and sodium stearyl fumarate.

Suitable binders for use in formulations of the invention include, but are not limited to: starch, for example, corn starch and pregelatinized starch; gelatin; sugars for example sucrose, glucose, dextrose and lactose; polyethylene glycol; waxes; and natural and synthetic gums, for example, acacia sodium alginate, polyvinylpyrrolidone, cellulosic polymers (for example, hydroxypropyl cellulose, hydroxypropyl methylcellulose, methyl cellulose, microcrystalline cellulose, ethyl cellulose, and hydroxyethyl cellulose).

Suitable disintegrants for use in a formulation of the invention include, for example, croscarmellose sodium (crosslinked sodium carboxymethylcellulose polymer), for example, the AC-Di-Sol® line of polymers available from FMC. It will be appreciated that other disintegrants may be employed to provide an effective disintegration system, for example, crospovidone, if they are used in accordance with the other aspects of the disintegration system described herein and not depart from the scope of the invention.

It will be appreciated that a formulation of the invention, once pressed into a tablet, may also include coloration and coating, for example, a coating comprising an Opady®, for example, Opady I, Opadry II, Opadry II HP.

Pharmaceutical formulations intended for the preparation of oral dosage forms (tablets and capsules) may further contain one or more agents selected from the group consisting of sweetening agents, flavoring agents, coloring agents and preserving agents in order to provide pharmaceutically elegant and palatable preparations.

In some formulations of the invention, when employed, precipitation inhibitors may be used in the range 10-40% w/w of the final formulation more preferably 20-40%; and more preferably in a range of from about 25 wt. % to about 35 wt., diluents/fillers may be used a levels of from about 5 wt. % to about 45 wt. %. disintegrants may be used in an amount of from about 2 wt. % to about 10 wt. % of the final formulation, antioxidants may be used in the range of about 0.1 wt. % to about 1 wt. % of the final formulation, binders may be used in the range of about 0.5 wt. % to about 10 wt. % of the final formulation.

In some embodiments it is preferred to press tablets having the following constituent weights:

| Component | Quantity/ Tablet (mg) | Amount for 3000 g (g) |
|---|---|---|
| Extrudate containing 4% of API (Compound of Formula 1) | 125.0 | 750.0 |
| Microcrystallme Cellulose | 88.90 | 533.40 |
| Polyethylene oxide (~M.W. of 500,000) PolyOX WSR Coagulant) | 75.0 | 450.0 |
| Polyethylene oxide (~M.W. of 200,000) PolyOX WSR 60K | 75.0 | 450.0 |
| Hypromellose Acetate Succinate (HPMCAS-MG) | 204.0 | 1224.0 |
| Croscarmellose Sodium | 30.0 | 180.0 |
| Magnesium Stearate | 1.50 | 9.0 |
| Butylated Hydroxytoluene (BHT) | 0.60 | 3.6 |
| Tablet weight | 600.0 | |

In some embodiments it is preferred to press tablets having the following constituent weights:

| Component | Quantity/ Tablet (mg) | Amount for 3450 g (g) |
|---|---|---|
| Extrudate containing 5% of API (Compound of Formula 1) | 100.00 | 600.00 |
| Microcrystalline Cellulose | 104.94 | 629.63 |
| Polyethylene oxide (~M.W. of 500,000) PolyOX WSR Coagulant) | 71.90 | 431.40 |
| Polyethylene oxide (~M.W. of 200,000) PolyOX WSR 60K | 71.90 | 431.40 |
| Hypromellose Acetate Succinate (HPMCAS-MG) | 195.50 | 1173.00 |
| Croscarmellose Sodium | 28.75 | 172.50 |
| Magnesium Stearate | 1.44 | 8.63 |
| Butylated Hydroxytoluene (BHT) | 0.58 | 3.45 |
| Tablet weight | 575.0 | |

In some embodiments it is preferred to press tablets having the following constituent weights:

| Component | Quantity/ tablet (mg) | Quantity/ 5000 g batch (g) |
|---|---|---|
| (Controlled Release Layer) | | |
| Extrudate containing 5.0% API (Compound of Formula 1) | 100.00 | 751.90 |
| Microcrystalline Cellulose | 112.10 | 842.90 |
| Polyethylene oxide (~M.W. of 500,000) | 33.25 | 250.00 |
| Polyethylene oxide (~M.W. of 200,000) | 38.00 | 285.70 |
| Hypromellose Acetate Succinate MG | 166.25 | 1250.00 |
| Croscarmellose Sodium | 23.75 | 178.60 |
| Magnesium Stearate | 1.19 | 8.90 |
| Butylated Hydroxytoulene | 0.47 | 3.50 |
| Weight of 12-hr controlled release layer | 475.0 | 3571.50 |
| (Immediate Release Layer) | | |
| Compound of Formula 1 | 5.0 | 35.7 |
| Povidone | 5.0 | 35.7 |
| Mannitol | 129.6 | 925.7 |
| Microcrystalline cellulose | 50.0 | 357.1 |

-continued

| Component | Quantity/tablet (mg) | Quantity/5000 g batch (g) |
|---|---|---|
| Croscarmellose Sodium | 10.0 | 71.4 |
| Magnesium Stearate | 0.40 | 2.9 |
| Weight of immediate release layer | 200.0 | 1428.5 |
| Total tablet weight | 675.00 | 5000.0 |

In some embodiments it is preferred to prepare an immediate-release formulation having the following constituent weights:

| Component | Quantity/tablet (mg) | Quantity/5000 g batch (g) |
|---|---|---|
| (Controlled Release Layer) | | |
| Extrudate containing 4.0% API (Compound of Formula 1) | 125.0 | 892.90 |
| Microcrystalline Cellulose | 98.15 | 701.10 |
| Polyethylene oxide (~M.W. of 500,000) | 35.0 | 250.00 |
| Polyethylene oxide (~M.W. of 200,000) | 40.0 | 285.70 |
| Hypromellose Acetate Succinate MG | 175.10 | 1250.70 |
| Croscarmellose Sodium | 25.0 | 178.60 |
| Magnesium Stearate | 1.25 | 8.90 |
| Butylated Hydroxytoulene | 0.5 | 3.60 |
| Weight of 12-hr controlled release layer | 500.0 | 3571.5 |
| (Immediate Release Layer) | | |
| Compound of Formula 1 | 5.0 | 35.7 |
| Povidone | 5.0 | 35.7 |
| Mannitol | 129.6 | 925.7 |
| Microcrystalline cellulose | 50.0 | 357.1 |
| Croscarmellose Sodium | 10.0 | 71.4 |
| Magnesium Stearate | 0.40 | 2.9 |
| Weight of immediate release layer | 200.0 | 1428.5 |
| Total tablet weight | 700.0 | 5000.0 |

Suitability of dosage forms intended for oral administration may be measured in a dissolution test, wherein the time-rate release of an amount of therapeutic compound dissolved into a standard media in a standard apparatus is measured after introducing the dosage form into the testing medium. In one aspect the invention provides a formulation adapted to preparing tablets comprising an extrudate of the invention, a disintegrant, a controlled release polymer(s), a precipitation inhibitor, and other excipients, for example, an antioxidant, a binder, a diluent and lubricant, are formulated using amounts of each that, once the formulation is pressed into a tablet having a hardness of from about 10 kP to about 20 kP, and in some embodiments, 12 kP to about 18 kP, provides a tablet with a release profile of FIG. 3 when subjected to dissolution testing.

In some embodiment, the formulation is pressed into a tablet which comprises about 5 mg of the API. In some embodiments the 5 mg tablet formulation provides the 12-hour release profile shown in FIG. 3A. In some embodiments a tablet containing 5 mg of API with the 12-hour release profile shown in FIG. 3A is combined with an immediate-release formulation containing up to 5 mg of API, which combined dosage form has the release profile shown in FIG. 3C. In some embodiments it is preferred to press an aliquot of the formulation containing 5 mg of API that provides the 12-hour release profile of FIG. 3A with an aliquot of an immediate release formulation in the form of a bilayer pressed tablet. In some embodiments it is preferred to provide the combination as a pressed tablet comprising an aliquot of the formulation containing 5 mg of API that provides the 12-hour release profile of FIG. 3A with a coating that provides 5 mg of API in an immediate-release formulation, which combination provides a release profile shown in FIG. 3C.

In some embodiments, formulations of the invention are directed to the preparation of tablet dosage forms. In some embodiments, formulations of the invention preferably will provide tablets in the rage of 10-20 kP hardness, more preferably 12-18 kP, and more preferably 15 kP hardness is preferred with a table weight of between 500 mg and 750 mg.

As mentioned above, the compounds of Formula I, and the formulations containing such compounds, are directed to treatment of movement disorders associated with Parkinson's Disease, and as such, a formulation providing sustained release and a long-duration therapeutic serum level is thought to be important in providing a therapeutic benefit to human patients to whom such a tablet is administered.

As is known, two qualities of tablet and capsule dosage forms important to release of an active pharmaceutical compound therefrom may be demonstrated using standard tests to measure the disintegration time and/or the dissolution time of the dosage form. A disintegration test measures the amount of time required for the dosage form to visibly disintegrate and wash out of a standard basket contained in a standard apparatus under standard operating conditions. A standard disintegration test is described for tablets and capsules in USP 31-NF26, Chapt. 701, beginning at p 266. There are equivalents thereto described in, for example, the European Pharmacopoeia and the Japanese Pharmacopoeia, which standard tests are generally accepted in the regulatory bodies of most countries. As the term is used herein with reference to formulations and tablets of the invention, "disintegration time" means: as determined in accordance with a test complying with the USP 31-NF26, Chapt. 701 standard run at 37° C. using aqueous HCl (pH 1.2) as a disintegration fluid.

In some embodiments, in addition to providing a sustained-release of the API, it is important to provide a "loading dose" by formulating some portion of the API in the dosage form into an immediate release formulation. In some embodiments it is preferred to provide a tablet formulated with a "bilayer" comprising in one layer the sustained-release formulation discussed above and in a second layer an immediate release formulation which provides a therapeutic serum level of the API within a short interval after dosing and thereafter provides a sustained period of API release that maintains therapeutic serum levels for 12 or 24 hours. The IR layer consists of a binder such as PVP, a disintegrant added intra-granulary and extra-granular such as sodium croscarmellose, fillers/compression aids such as microcrystalline cellulose added intra and extra-granular and mannitol added intra-granular and a lubricant such as magnesium stearate. In some embodiments it is preferred to formulate a bilayer tablet providing the release profile illustrated in FIG. 3C.

The preparation of formulations of the invention suitable for use in providing solid oral dosage forms comprising a composition of the invention may involve blending, roller compaction or wet granulation to densify and/or reduce the risk of segregation of components during subsequent handling (e.g., compression into tablets). Granulation steps can also be used to minimize the impact of raw material property variability (e.g., excipient particle size) on subsequent processing (e.g., tablet compression) and ultimate product performance. Lubrication is typically performed prior to roller compaction and tablet compression to reduce the tendency of material to adhere to compression surfaces (e.g., tablet tooling). In general lubricants are derivatives of stearic acid, for example, magnesium stearate or sodium stearly fumarate. Techniques and methods useful in preparation of dosage forms are know, for example, as described in Ansel, Introduction to Pharmaceutical Dosage Forms, Seventh Edition, 1999.

In general, preparation of oral dosage forms from pharmaceutical formulations of the invention requires that the pharmaceutical formulation of the invention (admixture of excipients, disintegrating system and composition of the invention) is compressed into a tablet or charged into a capsules. Tablets can be prepared with a variety of possible shapes (ellipsoidal, capsule, biconvex round, etc.). The powder can also be encapsulated in capsule dosage (e.g., using hard gelatin capsules). Techniques suitable for preparing solid oral dosage forms of the present invention are described in Remington's Pharmaceutical Sciences, 18th edition, edited by A. R. Gennaro, 1990, Chapter 89 and in Remington—The Science and Practice of Pharmacy, 21st edition, 2005, Chapter 45. In some embodiments of the present invention, it is preferred to prepare a tablet having a hardness of 16 kP or less, where the tablet has a target of providing the equivalent of 50 mg of a compound of Formula Ia (100% freebase), by placing 462.5 to 537.5 mg of the formulation into tableting tooling having an Elizabeth Carbide Die Company™ drawing number P-14305-B and pressing it in a Korsch™ tableting press.

With reference to FIG. 4, in general, compositions of the invention are prepared by dry-blending various excipients with milled dispersion (soluble polymer matrix comprising API dispersed therein), and compressing the blend to tablets.

There follows examples showing the preparation of compositions of the invention and which illustrates the effective release profile obtained from pharmaceutical formulations of the invention.

EXAMPLES

In the following examples the following common abbreviations are used for convenience: RT (room temperature, nominally 23° C.) is generally taken to be about 20° C. to 26° C.

Dissolution studies of the controlled release formulations of the invention were performed in the standard USP II dissolution apparatus (Distek) using a paddle method. The two-stage dissolution was conducted in 0.1N HCl for up to 0.5 hours in 800 ml of media followed by addition of 120 ml of 0.5M sodium phosphate tribasic buffer to result in a final solution pH of 6.8 and a final dissolution volume of 920 ml at a paddle speed of 75 rpm. To prepare the 0.5M sodium phosphate tribasic buffer –82.03 g of Sodium phosphate tribasic, anhydrous was added slowly into 500 mL of water while stirring the solution continuously. 500 mL of water was added and mixed well until completely dissolved. A fiber optic probe was immersed in the dissolution vessel to assess drug absorbance in real time as the drug gets released from the dosage form. The following parameters were employed to get the absorbance read:

Fiber-Optic Parameters:
Pathlength: 10 mm
No of scans: 3
Absorbance smoothing: 3
Exposure: 60 ms
Analytical wavelength: 262 nm
Average over range: 370-385 nm
Dissolution conditions:
Dissolution Bath: Distek
Apparatus: Paddle
Medium: 800 mL, deaerated 0.1N HCl for 30 minutes+120 mL of 0.5M Sodium phosphate tribasic to increase pH to 6.8 after 30 minute time point.
Bath temperature: 37.0° C.±0.5° C.
Paddle speed: 75 RPM Example IA and IB Preparation of an Extrudate of the Invention Comprising 4 wt. % API (IA) or 5 wt. % API (IB)

Example IA —A dispersion of the invention was prepared by combining 160 g of the compound of Formula IA and 2720 g of methacrylic acid copolymer Type B, NF (Eudragit® S-100) in alternating ⅓rd aliquots of the full weight of each component, starting with addition of the polymer, until the final third of the drug and the polymer were charged into the blender bin (Bohle blender MC 20). After addition the blender was operated for 15 minutes at 20 rpm. The blended material was subsequently charged to a Vector GMX-25 high shear granulator bowl and 1120 g of triethyl citrate were added to the bowl using a Watson Marlow 520DU peristaltic pump at a rate of 56 g/min at an impellar speed of 175 rpm, (no chopper). The plasticizer pre-blend is subsequently fed into a K-Tron KCL24T20 Feeder w/12 mm diameter 20 pitch screws gravimetric feeder connected to an Leistriz ZSE 18 HP twin screw extruder and the blend extruded. The feeder agitator of the extruder was operated at sufficient speed to provide an extrusion rate of 0.5 kg/hr at a screw speed of 40 rpm at a L/D ratio of 40:1. During the extrusion process, heat energy was supplied to the admixture while passing through the extruder from heating blocks secured along the barrel of the extruder. Power to the heating blocks was set to maintain a temperature of the extruder barrel at 155° C., as measured by thermocouples mounted inside of the extruder barrel. The hot melt extrudate was air cooled and pellitized. The extrudate was milled using a Fritz mill #DAS06 set up with a 0.050 inch screen run at 4600 rpm, then subsequently passed through a Fritz mill fitted with a 0.020 inch screen and the resulting extrudate sieved through a Kason Vibroscreen separator fitted with a 50 MG (280 microns) screen. The screened material (<280 microns) was collected for subsequent downstream operations. This material contained 4 wt. % API, 68 wt. % matrix polymer and 28 wt. % plasticizer In subsequent runs, extrudate was passed through chilled rollers rather than air-cooled. In some subsequent runs, extrudate was prepared using extrusion rates of up to 6 Kg/hr and L:D ratios of up to 25:1. In subsequent runs, the hot melt extrudate was prepared by metering the plasticizer (triethyl citrate) using an Eldex high pressure liquid metering pump at a flow rate of 5 ml/min directly into the feeding zone of the extruder via a liquid injection port while the drug/polymer blend is introduced through as K-Tron feeder to the extruder as in the previous runs.

Example IB —A second batch of extrudate was prepared using the same procedure as employed in IA—greater amounts of extrudate were employed to prepare 5 mg tablet formulations.

Example II

Preparation of a Continuous-Release Formulations, 12-Hr (Example IIA) and 24-hr (Example IIB)

The following procedure was employed to prepare tablet formulations comprising an extrudate of the invention, using the weights of the constituents shown in the tables below:

The full weight of AQOAT AS-MG (HPMCAS-MG), NF used in the formulation was fed through a Fitzmill using a 0.050" screen, then the milled material was passed through the Fitzmill using a 0.020" screen to get HPMCAS-MG-NF-0.020". Separately, butylated hydroxytoluene (BHT) is passed thorough the Comil. assembled with a 2A018R01530 screen and 2A1601173 impeller.

The full weight of sieved extrudate, as prepared in Example I, was charged into a 10 L Bohle blender, followed by addition, in order, of the full weight of Polyox WSR Coagulant LEO NF (which had been sieved through a 30 mesh screen); Polyox WSR 60K NF (which had been sieved through a 30 mesh screen); microcrystalline cellulose, AQOAT AS-MG (HPMCAS-MG)-NF (which had been sieved through a 0.020" screen); croscarmellose sodium (which had been sieved through a 30 mesh screen) and BHT. The Bohle blender was operated for 15 minutes at a speed of 25 rpm. This was followed by addition to the batch of magnesium stearate (previously sifted through a 30 mesh screen) and the blender was operated for an additional 1 minute at 25 rpm In a first run, the following constituents were employed in the table formulation, intended as a 12-hr continuous-release formulation (Example IIA):

| Component | Intended Quantity/Tablet (mg) | Weight in Run (g) |
| --- | --- | --- |
| Extrudate containing 4% of API (from Example IA above) | 125.0 | 750.0 |
| Microcrystalline Cellulose | 98.15 | 588.9 |
| Polyethylene oxide (~M.W. of 500,000) PolyOX WSR Coagulant | 35.0 | 210.0 |
| Polyethylene oxide (~M.W. of 200,000) PolyOX WSR 60K | 40.0 | 240.0 |
| Hypromellose Acetate Succinate (HPMCAS-MG) | 175.10 | 1050.6 |
| Croscarmellose Sodium | 25.0 | 150.0 |
| Magnesium Stearate | 1.25 | 7.5 |
| Butylated Hydroxytoluene (BHT) | 0.5 | 3.0 |
| Tablet weight | 500.0 | |

In a second run, the following constituents were employed in the table formulation, intended as a 24-hr continuous-release formulation (Example IIB):

| Component | Intended Quantity/Tablet (mg) | Weight in Run (g) |
| --- | --- | --- |
| Extrudate containing 5% of API (from Example IB above) | 100.00 | 631.57 |
| Microcrystalline Cellulose | 112.10 | 707.99 |
| Polyethylene oxide (~M.W. of 500,000) PolyOX WSR Coagulant | 33.25 | 210.00 |
| Polyethylene oxide (~M.W. of 200,000) PolyOX WSR 60K | 38.00 | 240.00 |
| Hypromellose Acetate Succinate (HPMCAS-MG) | 166.25 | 1049.99 |
| Croscarmellose Sodium | 23.75 | 150.00 |
| Magnesium Stearate | 1.19 | 7.50 |
| Butylated Hydroxytoluene (BHT) | 0.47 | 2.97 |
| Tablet weight | 475.0 | |

Tablets were prepared by pressing a 500 mg of Formulation IA (Tablet IA) or 600 mg of Formula IB (Tablet IB) in a 0.625"×0.3125" modified oval tablet die, yielding a tablet with a hardness of 15±3 kP in each case.

Example III

Preparation of a Bilayer Tablet

The following procedure was employed to prepare an immediate release tablet a formulation comprising the compound of Formula IA:

Into a high shear granulation process (GEA Aeromatic Fielder PMA 25, was charged 35.7 g of the compound of Formula IA, 925.7 g mannitol, 128.6 g microcrystalline cellulose, and 37.5 g croscarmellose sodium. The granulator was operated for 3.5 minutes using an impellar speed of 240 rpm and chopper speed of 3000 rpm to dry-blend the materials. The dry-blended materials were wet mixed with addition of the granulating fluid (polyvinylpyrollidone solution) over 9.5 minutes using an impellar speed of 220 rpm and chopper speed of 1500 rpm. The granulating fluid was added at a spray rate of 350 g/min. After wet mixing the granulated material was dried in a fluid bed dryer (GEA Niro MP 2/3) until an LOD≤2.0 was obtained.

The dried granules were blended with 228.5 g microcrystalline cellulose and 35.7 g croscarmellose sodium for 5 minutes at 30 rpm and then for an another 2 minutes at 25 rpm after addition of 2.9 g of magnesium stearate, to provide a formulation for use in preparing an "immediate-release" layer of a bilayer tablet.

Preparation of Bilayer Tablet

In a first run, tablets were prepared using 500 mg of the formulation of Example IIA was pressed into a first tablet layer using a 0.625"×0.3125" modified oval tooling tablet die. To this was added 200 mg of the "immediate-release" formulation prepared above to provide a 700 mg bilayer tablet (Example IIIA-700 mg bilayer tablets).

In a second run, tablets were prepared using 475 mg of the formulation of Example IIA was pressed into a first tablet layer using a 0.625"×0.3125" modified oval tooling tablet die. To this was added 200 mg of the "immediate-release" formulation prepared above to provide a 675 mg bilayer tablet (Example IIIA-675 mg bilayer tablets).

Example IV

Dissolution Testing of Tablets

The tablets prepared above (Example IIA, Example IIB, Example IIIA) were subjected to the dissolution tests described herein. These tablets gave the results shown in FIGS. 3A through 3C, demonstrating nearly complete release of a compound of Formula IA at therapeutic levels over 12 and 24 hours respectively.

Example V

The tablets prepared in Examples II and III above were administered to human subjects in the following manner:

A randomized, single-dose, four-period, four-treatment, four-way, crossover study under fasted conditions comparing the test and reference products. The primary objective of this study was to compare the pharmacokinetics of compound IA following administration of three different release prototypes of once-daily (QD) formulation tablets: (1) 12 hr Control Release (CR), (2) 24 hr CR and (3) Bi-Layer (combined IR/CR); and an immediate release (IR) (reference) tablet formulation.

The study was conducted with 16 (14 completing) healthy adult subjects in accordance with Protocol No. P08199. A single dose of Compound I (2×5 mg 12 hr CR tablets, 2×5 mg 24 hr CR tablets, 1×5 mg/5 mg IR/CR Bi-Layered tablet or 1×10 mg IR tablet) was administered to all subjects following an overnight fast of at least 10 hours in each study period. Test Treatment A was Compound I 5 mg 12 hr CR Tablets, Test Treatment B was Compound IA, 5 mg 24 hr CR Tablets (Merck Research Laboratories), Test Treatment C was Compound IA, 5 mg/5 mg IR/CR Bi-Layer Tablets and Reference Treatment D was Compound IA 10 mg IR tablets. The subjects received the test products in three of the study periods and the reference product in the other study period according to a four-treatment, four-sequence randomization schedule. There was a washout interval of 5 days between dosing in each study period. This study was conducted under Investigational New Drug application #64,558.

Blood samples were collected pre-dose and at intervals over 24 hours after each dose. The plasma samples for all subjects were determine dusing a validated LC-MS/MS assay. A total of 16 healthy, adult subjects were enrolled, and 14 subjects completed the study. All analyses were performed and all tables, figures, and data listings were prepared using SAS, Version 9.2.

PK Analysis: Fifteen (15) blood samples were collected from each subject; within 60 minutes prior to dosing then at 0.25, 0.5, 0.75, 1, 1.25, 1.5, 2, 3, 4, 5, 6, 12, 18, and 24 hours after dosing for analysis of plasma concentrations of compound IA. The analytical data was used to calculate the PK parameters: AUC0-t, AUC0-inf, Cmax, Tmax, Ke and T½. The t in AUC0-t is the time at which the last quantifiable concentration was recorded. The Statistical Analysis System (SAS, Version 9.2) was used for all PK and statistical calculations.

Descriptive statistics are provided for the concentration data at each sampling time and the derived pharmacokinetic parameters. Descriptive statistics comprised number of observations (n), arithmetic mean, standard deviation, coefficient of variation, geometric mean, minimum, median and maximum.

Statistical Methods:

Individual plasma compound IA concentration data were used to estimate the following primary pharmacokinetic variables, after single doses of compound IA given as CR 12 hour, CR 24 hour, IR/CR Bi-Layer, or IR formulations for the determination of bioavailability and characterization of the pharmacokinetics.

AUC0-t Area under the concentration-time curve from time 0 to the time of the last measurable sample
Cmax Maximum observed plasma concentration
Tmax Time to maximum observed plasma concentration
AUC∞ Area under the concentration-time curve from time 0 to infinity after single dosing
t½ Terminal phase (elimination) half-life PK Analysis: Fifteen (15) blood samples were collected from each subject; within 60 minutes prior to dosing then at 0.25, 0.5, 0.75, 1, 1.25, 1.5, 2, 3, 4, 5, 6, 12, 18, and 24 hours after dosing for analysis of plasma compound IA concentrations. The analytical data was used to calculate the PK parameters: AUC0-t, AUC0-inf, Cmax, Tmax, Ke and T½. The t in AUC0-t is the time at which the last quantifiable concentration was recorded. The Statistical Analysis System (SAS, Version 9.2) was used for all PK and statistical calculations.

Descriptive statistics are provided for the concentration data at each sampling time and the derived pharmacokinetic parameters. Descriptive statistics comprised number of observations (n), arithmetic mean, standard deviation, coefficient of variation, geometric mean, minimum, median and maximum.

Statistical Methods:

Individual plasma compound IA concentration data were used to estimate the following primary pharmacokinetic variables, after single doses of compound IA given as CR 12 hour, CR 24 hour, IR/CR Bi-Layer, or IR formulations for the determination of bioavailability and characterization of the pharmacokinetics.

AUC0-t Area under the concentration-time curve from time 0 to the time of the last measurable sample
Cmax Maximum observed plasma concentration
Tmax Time to maximum observed plasma concentration
AUC∞ Area under the concentration-time curve from time 0 to infinity after single dosing
t½ Terminal phase (elimination) half-life

TABLE 2.1

Summary of Pharmacokinetic Parameters Untransformed Data

| Pharmacokinetic Parameter | Geometric mean ± SD (% CV) | | | |
| --- | --- | --- | --- | --- |
| | Treatment A[1] (N = 15)* | Treatment B[2] (N = 14)* | Treatment C[3] (N = 14)* | Treatment D[4] (N = 15)* |
| AUC0-24 (ng · hr/mL) | 368.172 ± 1.480 (0.408) | 299.400 ± 1.463 (0.395) | 470.465 ± 1.598 (0.496) | 556.646 ± 1.604 (0.500) |
| AUC0-inf (ng · hr/mL) | 570.394 ± 1.381 (0.332) | 448.341 ± 1.369 (0.322) | 563.377 ± 1.545 (0.457) | 683.964 ± 1.445 (0.381) |
| Cmax (ng/mL) | 57.792 ± 1.501 (0.423) | 36.378 ± 1.505 (0.426) | 77.727 ± 1.699 (0.570) | 169.910 ± 1.681 (0.557) |
| Ke (1/hr) | 0.053 ± 1.856 (0.683) | 0.061 ± 1.616 (0.509) | 0.077 ± 1.850 (0.678) | 0.117 ± 1.717 (0.582) |
| C12 (ng/mL) | 9.851 ± 1.947 (0.747) | 9.508 ± 1.799 (0.642) | 9.968 ± 1.909 (0.720) | 5.290 ± 2.397 (1.071) |
| C24 (ng/mL) | 6.971 ± 1.689 (0.562) | 8.954 ± 1.548 (0.459) | 3.890 ± 1.765 (0.617) | 2.212 ± 2.677 (1.280) |

TABLE 2.1-continued

Summary of Pharmacokinetic Parameters Untransformed Data

| Pharmacokinetic Parameter | Treatment A[1] (N = 15)* | Treatment B[2] (N = 14)* | Treatment C[3] (N = 14)* | Treatment D[4] (N = 15)* |
|---|---|---|---|---|
| | Geometric mean ± SD (% CV) | | | |
| | Median (Minimum-Maximum)[5] | | | |
| $T_{1/2}$ (hr) | 10.964 (6.784-33.821) | 11.961 (8.050-15.872) | 7.560 (4.563-46.679) | 5.539 (2.012-17.368) |
| Tmax (hour) | 3.000 (2.000-18.000) | 4.500 (3.000-12.000) | 1.000 (0.750-5.000) | 1.000 (0.500-2.000) |

*N = 10 for AUC0-inf, Ke, and T½ for Treatment A; N = 2 for AUC0-inf, Ke, and T½ for Treatment B; N = 13 for AUC0inf, Ke, and T½ for Treatment C; N = 12 for AUC0-inf, Ke, andT½ for Treatment D
[1]treatment A (test): Single dose of 2 × 5 mg SCH 420814 (preladenant) 12 hr CR tablet
[2]treatment B (test): Single dose of 2 × 5 mg SCH 420814 (preladenant) 24 hr CR tablet
[3]treatment C (test): Single dose of 10 mg SCH 420814 (preladenant) IR/CR tablet
[4]treatment D (reference): Single dose of 10 mg SCH 420814 (preladenant) IR tablet
[5]Geometric means are not considered an appropriate estimate for the parameters T½ and Tmax. Instead of the geometric mean, SD, and CV; the median, minimum, and maximum values are reported for these parameters.

As can be seen from the table, formulations of the invention provided sustained release of the API with improved trough-levels and therapeutic exposure over a 12 or 24 hour period. The bilayer tablet provided satisfactory serum levels for therapeutic use.

Figure 2A:
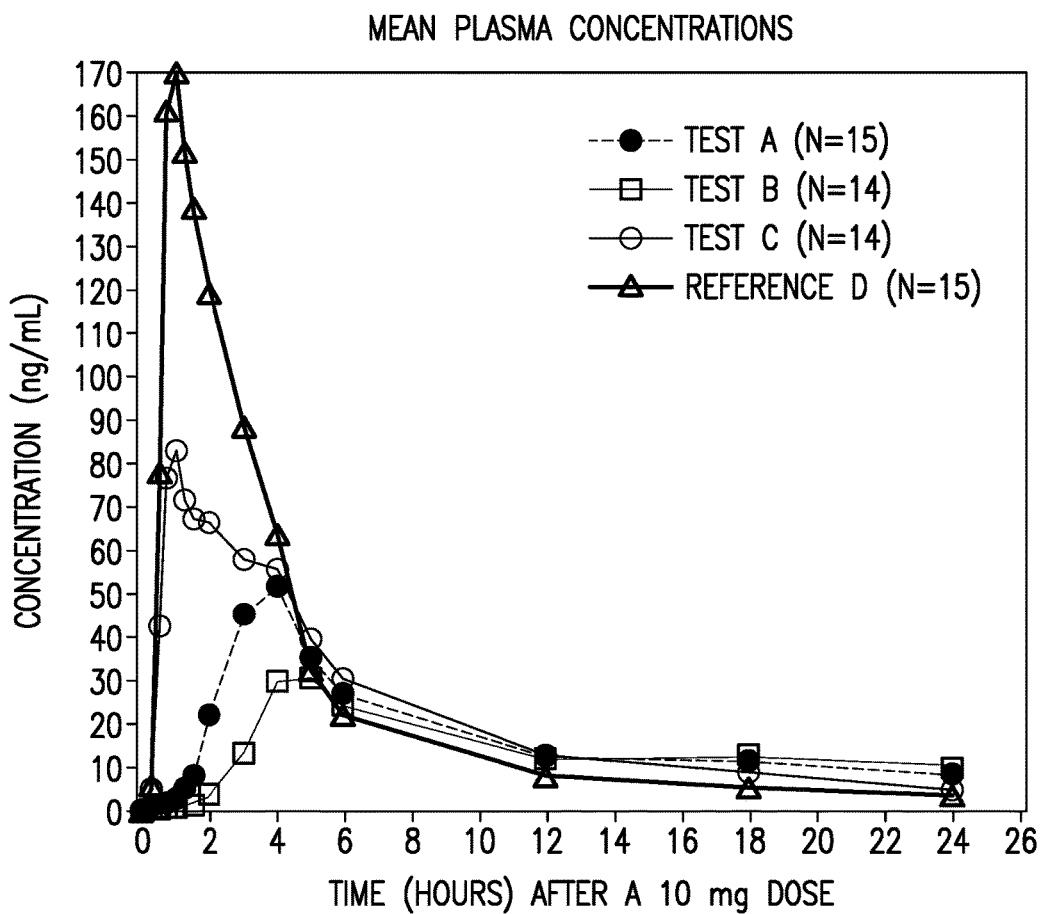
FIG. 2A: AUC profile for Tablets of the Invention following a 10 mg dose.
Figure 2B:
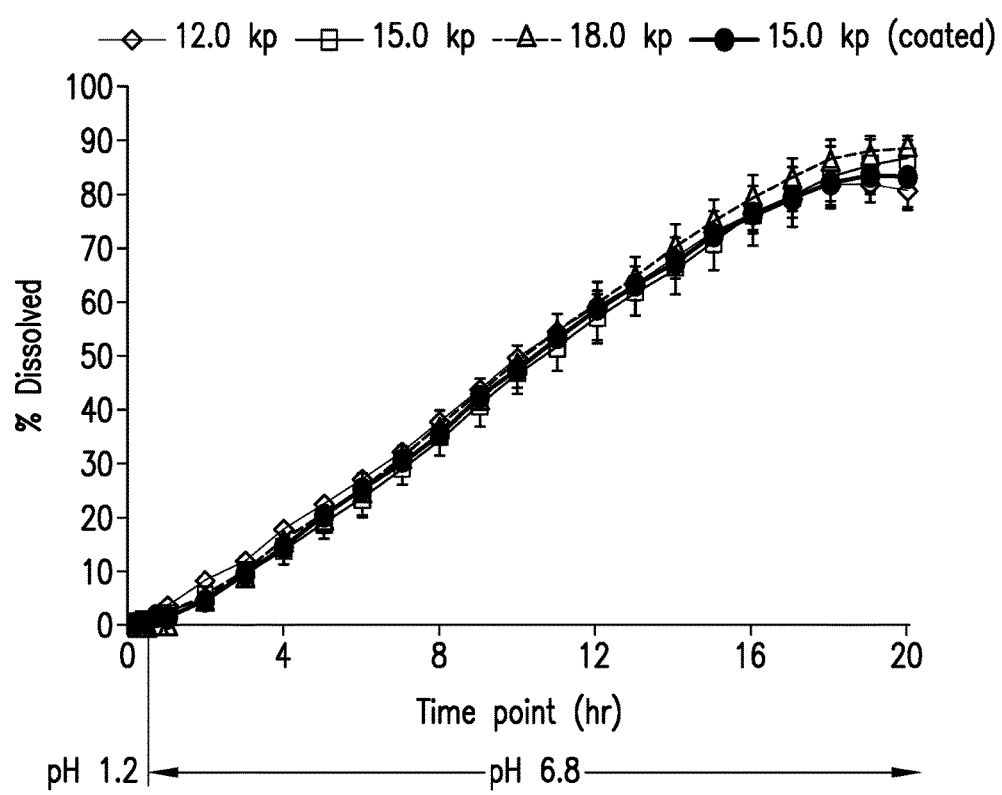
FIG. 2B: Dissolution profile of 20 hr release tablet showing that the tablet hardness (12-18 kp).

As can be seen from FIG. 2B, tablet hardness does not influence dissolution profile from the CR tablets.

The foregoing examples are meant to be illustrative and not limiting.

What is claimed is:

1. A dispersion comprising a compound of Formula IA or a salt thereof:

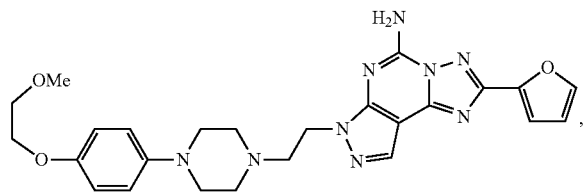

Formula IA a plasticizer and a matrix polymer, wherein said matrix polymer is: (a) a polymer made from free-radical polymerization of methacrylic acid and methylmethacrylate in a 1:2 ratio, and having an average molar mass of approximately 125,000 g/mol; or (b) a polymer made from free radical polymerization of a 1:1 mixture of methacrylic acid and ethylacrylate, and having a weight average molecular mass of approximately 320 Kg/mol.

2. The dispersion of claim 1, wherein said compound of Formula IA and is present in the amount of about 5 wt. %, said plasticizer is triethylcitrate and is present in the amount of about 25 wt.%, and said matrix polymer is methacrylic acid/methacrylate 1:2 ratio and is present in an amount of about 70 wt.%.

3. A formulation comprising: (i) the polymer dispersion of claim 2; (ii) one or more controlled-release polymers; and (iii) a precipitation inhibitor.

4. The formulation of claim 3, further comprising one or more of a glidant; binder; anti-oxidant; compression aid, disintegrant or lubricant.

5. A tablet prepared from the formulation of claim 4 having a target hardness of 15 ±3 kp.

6. The tablet of claim 5 which comprises about 5 mg of the compound of Formula IA.

7. The tablet of claim 5 which comprises about 10 mg of the compound of Formula IA.

8. The tablet of claim 6 which is further combined with an immediate-release formulation comprising about 5 mg of the compound of Formula IA.

9. The tablet of claim 6 which provides the release profile of FIG. 3A.

10. The tablet of claim 7 which provides the release profile of FIG. 3B.

11. The tablet of claim 8 which provides the release profile of FIG. 3C.

12. A tablet having the constituent ratio of either Table X, Y or Z:

TABLE X

| Component | Quantity/ Tablet (mg) | Amount for 3000 g (g) |
|---|---|---|
| Extrudate containing 4% of API (Compound of Formula 1) | 125.0 | 750.0 |
| Microcrystalline Cellulose | 88.90 | 533.40 |
| Polyethylene oxide (~M.W. of 500,000) PolyOX WSR Coagulant) | 75.0 | 450.0 |
| Polyethylene oxide (~M.W. of 200,000) PolyOX WSR 60K | 75.0 | 450.0 |
| Hypromellose Acetate Succinate (HPMCAS-MG) | 204.0 | 1224.0 |
| Croscarmellose Sodium | 30.0 | 180.0 |
| Magnesium Stearate | 1.50 | 9.0 |
| Butylated Hydroxytoluene (BHT) | 0.60 | 3.6 |
| Tablet weight | 600.0. | |

TABLE Y

| Component | Quantity/ Tablet (mg) | Amount for 3450 g (g) |
|---|---|---|
| Extrudate containing 5% of API (Compound of Formula 1) | 100.00 | 600.00 |
| Microcrystalline Cellulose | 104.94 | 629.63 |
| Polyethylene oxide (~M.W. of 500,000) PolyOX WSR Coagulant) | 71.90 | 431.40 |
| Polyethylene oxide (~M.W. of 200,000) PolyOX WSR 60K | 71.90 | 431.40 |

TABLE Y-continued

| Component | Quantity/ Tablet (mg) | Amount for 3450 g (g) |
|---|---|---|
| Hypromellose Acetate Succinate (HPMCAS-MG) | 195.50 | 1173.00 |
| Croscarmellose Sodium | 28.75 | 172.50 |
| Magnesium Stearate | 1.44 | 8.63 |
| Butylated Hydroxy toluene (BHT) | 0.58 | 3.45 |
| Tablet weight | 575.0. | |

TABLE Z

| Component | Quantity/ tablet (mg) | Quantity/ 5000 g batch (g) |
|---|---|---|
| (Controlled Release Layer) | | |
| Extrudate containing 5.0% API (Compound of Formula 1) | 100.00 | 751.90 |
| Microcrystalline Cellulose | 112.10 | 842.90 |
| Polyethylene oxide (~M.W. of 500,000) | 33.25 | 250.00 |
| Polyethylene oxide (~M.W. of 200,000) | 38.00 | 285.70 |
| Hypromellose Acetate Succinate MG | 166.25 | 1250.00 |

TABLE Z-continued

| Component | Quantity/ tablet (mg) | Quantity/ 5000 g batch (g) |
|---|---|---|
| Croscarmellose Sodium | 23.75 | 178.60 |
| Magnesium Stearate | 1.19 | 8.90 |
| Butylated Hydroxytoulene | 0.47 | 3.50 |
| Weight of 12-hr controlled release layer | 475.0 | 3571.50 |
| (Immediate Release Layer) | | |
| Compound of Formula 1 | 5.0 | 35.7 |
| Povidone | 5.0 | 35.7 |
| Mannitol | 129.6 | 925.7 |
| Microcrystalline cellulose | 50.0 | 357.1 |
| Croscarmellose Sodium | 10.0 | 71.4 |
| Magnesium Stearate | 0.40 | 2.9 |
| Weight of immediate release layer | 200.0 | 1428.5 |
| Total tablet weight | 675.00 | 5000.0. |

13. A tablet of the constituents of Table X of claim 12 which is combined with an immediate release formulation comprising about 5 mg of a compound of Formula IA.

* * * * *